United States Patent [19]
Maniar et al.

[11] Patent Number: 5,846,525
[45] Date of Patent: Dec. 8, 1998

[54] PROTECTED BIOPOLYMERS FOR ORAL ADMINISTRATION AND METHODS OF USING SAME

[75] Inventors: Manoj Maniar; Steven Mauch, both of San Diego, Calif.

[73] Assignee: Trega Biosciences, Inc., San Diego, Calif.

[21] Appl. No.: 574,556

[22] Filed: Dec. 19, 1995

[51] Int. Cl.$^6$ .......................... A61K 47/32; A61K 38/19
[52] U.S. Cl. ........................................ 424/78.12; 424/78.1
[58] Field of Search ................................ 424/78.1, 78.12

[56] References Cited

U.S. PATENT DOCUMENTS 5,288,503   2/1994   Wood et al. ............................ 424/78.1

OTHER PUBLICATIONS

U.K. 665,073 Jan. 1952.

*Primary Examiner*—Peter F. Kulkosky
*Attorney, Agent, or Firm*—Campbell & Flores LLP

[57] ABSTRACT

The present invention provides a composition comprising an ion exchange resin and a therapeutically active biopolymer in a form for oral administration. The present invention also provides a composition comprising Amberlite® IRP-64 and a cytokine regulatory agent having the amino acid sequence:

Ac-Nle-Gln-His-(D)Phe-Arg-(D)Trp-Gly-NH$_2$, in a form for oral administration. The present invention further provides a method of protecting a therapeutically active biopolymer from degradation by forming a complex of the biopolymer and an ion exchange resin. In addition, the present invention provides a method of reducing or inhibiting the severity of a pathological condition by orally administering a therapeutically effective dose of the composition.

14 Claims, No Drawings

PROTECTED BIOPOLYMERS FOR ORAL ADMINISTRATION AND METHODS OF USING SAME

BACKGROUND OF THE INVENTION

FIELD OF THE INVENTION

This invention relates generally to the fields of biopolymer chemistry and drug delivery and, more specifically, to compositions containing a protected biopolymer and methods of their use.

BACKGROUND INFORMATION

Biopolymers such as nucleic acids, peptides, polypeptides and proteins are finding use as therapeutic agents for treating various diseases. To obtain a desired-therapeutic effect, an effective amount of a therapeutically active biopolymer must be delivered to the diseased area. The biopolymer can be administered by local or systemic injection, or can be applied directly to the diseased area. However, these methods of administration can be inconvenient and can require assistance. Such methods also are unsuitable for long-term therapy, which can last for several years. Thus, a delivery system that allows a patient to administer the biopolymer without the need for injections and without assistance is desirable.

Oral administration would be a convenient method of delivering a therapeutically active biopolymer to a subject. Unfortunately, acids and digestive enzymes in the stomach and small intestine can degrade a biopolymer, rendering it inactive. As a result, only a fraction of an orally administered biopolymer ultimately reaches the large intestine, where it can be absorbed into the circulation and transported to the diseased tissue.

Various approaches have attempted to address the problems of using oral administration to deliver a therapeutically effective amount of biopolymer to the large intestine. For example, attempts have been made to compensate for the degradation of the biopolymer in the stomach and small intestine by increasing the amount or frequency of oral administration. Unfortunately, these approaches require administering large amounts of the biopolymer, which can cause undesirable side-effects in the mouth, esophagus or gastrointestinal tract. Moreover, it can be time consuming and expensive to prepare a sufficient amount of biopolymer necessary for repeated high dose administrations.

Thus, a need exists for a therapeutically active biopolymer in an orally administrable form, such that the therapeutically active biopolymer is stabilized from degradation in the stomach and small intestine. The present invention satisfies this need and provides related advantages as well.

SUMMARY OF THE INVENTION

The present invention provides a composition comprising an ion exchange resin and a therapeutically active biopolymer in a form for oral administration. The composition of matter can be in an amount that provides a therapeutically effective dose. In one embodiment, the therapeutically active biopolymer can be a nucleic acid, a peptide, a polypeptide or a protein. In another embodiment, the invention provides a composition comprising an ion exchange resin and a peptide such as a cytokine regulatory agent having the amino acid sequence $X_1$-$X_2$-(D)Phe-Arg-(D)Trp-$X_3$, where $X_1$, $X_2$ and $X_3$ each can be an amino acid or amino acid analog. As disclosed herein, a composition of the invention also can be coated, if desired. In a further embodiment, the invention provides a composition comprising Amberlite® IRP-64 and a cytokine regulatory agent having the amino acid sequence:

Ac-Nle-Gln-His-(D)Phe-Arg-(D)Trp-Gly-$NH_2$, in a form for oral administration.

In addition, the invention provides a method of protecting a therapeutically active biopolymer from degradation by forming a complex comprising the therapeutically active biopolymer and an ion exchange resin. The invention further provides a method of reducing or inhibiting the severity of a pathological condition, comprising orally administering a therapeutically effective dose of the composition to a subject. In one embodiment, the pathological condition is characterized, in part, by altered or aberrant cytokine activity.

DETAILED DESCRIPTION OF THE INVENTION

The present invention provides a composition comprising an ion exchange resin and a therapeutically active biopolymer in a form for oral administration. As used herein, the term "biopolymer" means a molecule such as a peptide, polypeptide, protein, nucleic acid, nucleoprotein or the like. A biopolymer is characterized, in part, by containing repeated subunits such as amino acids or nucleotides, which can be the same or different. When used in reference to a biopolymer, the term "therapeutically active" means that the biopolymer can effectively reduce or inhibit the severity of a pathological condition or can provide a nutritional supplement. As used herein, the term "pathological condition" is used in its broadest sense to include an abnormal physiological state as occurs, for example, in a subject suffering from a disease or a nutritional or physical deficiency.

A composition of the invention is in a form for oral administration. Such a form can be a liquid form or solid form and can include a pharmaceutically acceptable carrier (see U.S. Pat. No. 5,344,825, which is incorporated herein by reference). For example, the composition can be a liquid suspension or an emulsion, which is in the form of a syrup or drops. A composition of the invention also can be in a solid form such as a granule, a tablet, a dragee, a capsule or a sachet. A granule is a solid preparation comprising small particles of the composition of the invention and an excipient such as lactose, mannitol, microcrystalline cellulose or talc. A tablet is obtained by directly compressing a composition of the invention, which can be in granular form, with an excipient. A capsule is a container, such as a gelatin shell, for a composition of the invention, and can be a dry-filled, wet-filled, liquid-filled or granule-filled shell. Sachets are receptacles that contain a composition of the invention, such that the composition can be removed directly after opening the sachet. A solid form can be of different shapes, sizes or colors depending, for example, on the type and amount of composition of the invention and excipient it contains.

A composition of the invention in a form for oral administration also can contain a pharmaceutically acceptable carrier, which can be an aqueous solution such as physiologically buffered saline, or a vehicle such as a glycol, glycerol or an oil such as olive oil or organic esters. A pharmaceutically acceptable carrier can contain a physiologically acceptable compound that acts, for example, to stabilize or increase the absorption of the therapeutically active biopolymer. Such physiologically acceptable compounds include, for example, carbohydrates such as glucose, sucrose or dextrans, antioxidants such as ascorbic acid or glutathione, chelating agents or other stabilizers or excipients. One skilled in the art would know that the choice of a pharmaceutically acceptable carrier depends, in part, on the particular physical or chemical characteristics of the specific biopolymer.

A composition of the invention can be in an amount that provides a therapeutically effective dose. As used herein, the term "therapeutically effective dose" means an amount of the composition that is sufficient to alleviate a pathological condition in a subject or to prevent or delay onset or recurrence of a pathology. As used herein, the term "therapeutically effective dose" is in contrast to the amount of a composition of an ion exchange resin and a therapeutically active biopolymer present during a nontherapeutic applications. As is well known, peptides, polypeptides, proteins or nucleic acids can bind to ion exchange resins for nontherapeutic purposes, for example preparation such as batch adsorption or concentration, purification such as column chromatography, or analysis such as analytical HPLC. Under such nontherapeutic applications, the ion exchange resin and therapeutically active biopolymer are not in a therapeutically effective dose; moreover, they are not in a form for oral administration. The present invention is distinguished from compositions in such nontherapeutic applications in that such compositions are neither in "a form for oral administration" nor "a therapeutically effective dose."

The amount of a composition of the invention required to provide a therapeutically effective dose of a biopolymer depends on a variety of factors, including the particular characteristics of the therapeutically active biopolymer, the type and severity of the pathological condition and the patient's medical condition. Based on such factors, a skilled physician can readily determine and prescribe the therapeutically effective dose of a composition of the invention.

A therapeutically active biopolymer useful in the invention can be a nucleic acid, which can be a single stranded or double stranded oligonucleotide or polynucleotide, which can be a DNA such as a cDNA, or a RNA such as a ribozyme. A nucleic acid can consist of naturally occurring bases such as adenine, guanine, cytosine, thymine or uracil, or can consist of base analogs. In addition, a nucleic acid can have a typical phosphodiester backbone or can have, for example, a thioester linkage, which can minimize the effects of nucleases on the nucleic acid in vitro or in vivo. Methods for synthesizing nucleic acids are well known in the art and are described, for example, in Sambrook et al., *Molecular Cloning: A Laboratory Manual*, Cold Spring Harbor Press, Cold Spring Harbor, N.Y. (1989), which is incorporated herein by reference. Synthetic nucleic acids also are available from various commercial sources.

It can be useful to orally administer a double stranded nucleic acid for delivery to the small or large intestine, for example, to modulate the expression of cellular gene products or to treat pathological conditions such as colon cancer. A composition comprising an ion exchange resin and a nucleic acid such as a viral vector can be useful in gene therapy to deliver the nucleic acid to the small or large intestine, thereby targeting the vector to the desired tissue. If desired, the nucleic acid can be present in an expression vector, which can be selected to produce an antisense RNA or a ribozyme for delivery to the small or large intestine (see Godson et al., *J. Biol. Chem.* 268:11946–11950 (1993); Reed et al., *Canc. Res.* 50:6565–6570 (1990a); Reed et al., *Proc. Nat'l Acad. Sci., USA* 87:3660–3664 (1990b), each of which is incorporated herein by reference). Homologous recombinant gene knock-out can be used to reduce the expression of a gene product in a cell (see Capecchi, *Nature* 344:105 (1990) and references cited therein; McCall et al., *Proc. Nat'l Acad. Sci., USA* 89:5710–5714 (1992), each of which is incorporated by reference herein). Similarly, a single stranded nucleic acid such as a ribozyme or an antisense oligonucleotide also can be used to modulate expression in cells or treat a pathological condition.

A therapeutically active biopolymer useful in the invention also can be a peptide, polypeptide or protein. The Dictionary of Biochemistry and Molecular Biology (2nd ed. 1989, J. Stenesh, ed.) provides the following three definitions. A "peptide" is a linear compound that consists of two or more amino acids that are linked by means of peptide bonds. A "polypeptide" is a linear polymer of more than 10 amino acids that are linked by means of peptide bonds. A "protein" is a high molecular weight polypeptide of (L)-amino acids that is synthesized by living cells.

As used herein, the term "amino acid" is used in its broadest sense to mean a naturally occurring (L)-amino acid; a non-naturally occurring amino acid such as a (D)-amino acid; an amino acid such as norleucine, norvaline or the like; a chemically modified amino acid such as an amino acid analog; or a mimetic, which can be an organic molecule known in the art to have properties characteristic of an amino acid. An example of such an amino acid is a mimetic of phenylalanine that allows the same conformational restriction of a peptide as would (L)-phenylalanine. Examples of such amino acids can be found, for example, in Roberts and Vellaccio, *The Peptides: Analysis, Synthesis, Biology*, Eds. Gross and Meinhofer, Vol. 5, p. 341, Academic Press, Inc., New York, N.Y. (1983), which is incorporated herein by reference). Methods for synthesizing peptides, polypeptides and proteins are well known in the art (see, for example, U.S. Pat. No. 5,420,109; M. Bodanzsky, *Principles of Peptide Synthesis* (1st ed. & 2d rev. ed.), Springer-Verlag, New York, N.Y. (1984 & 1993), see Chapter 7; Stewart and Young, *Solid Phase Peptide Synthesis*, (2d ed.), Pierce Chemical Co., Rockford, Ill. (1984), each of which is incorporated herein by reference).

As disclosed herein, a peptide such as a cytokine regulatory agent is particularly useful in formulating a composition of the invention. A cytokine regulatory agent ("CRA") is a peptide that can regulate the level or activity of a cytokine. Cytokines are a class of secreted proteins that regulate a variety of cellular interactions. In general, cytokines are immunoregulatory proteins that mediate host defense responses, cell regulation and cell differentiation (see, for example, Chapter 13, Kuby, *Immunology* (2d ed.) W. H. Freeman and Co. (1994); and U.S. Pat. No. 5,420,109, each which is incorporated herein by reference). In response to many different inducing stimuli, including an environmental, mechanical or pathological stress, various cells secrete cytokines. In turn, the secreted cytokines regulate the immune response by controlling host defense responses, cell proliferation, differentiation and effector functions. Cytokines are well known in the art and include the tumor necrosis factors (TNFs); colony stimulating factors (CSFs); interferons (IFs); interleukins such as IL-1, IL-2, IL-3, IL-4, IL-5, IL-6, IL-7, IL-8, IL-9, IL-10, IL-11, IL-12, IL-13, IL-14 and IL-15; transforming growth factors (TGFs); oncostatin M (OSM); leukemia inhibiting factor (LIF); and platelet activating factor (PAF).

Cytokines normally are present in very low amounts in a tissue and their effects are mediated through binding to high affinity receptors on specific cell types. The level of a cytokine can increase or decrease in a tissue at different times following induction of an immune, inflammatory, repair or acute phase response. Cytokines can regulate the immune response through immunostimulatory or immunosuppresive effects. For example, IL-10 can block activation of many inflammatory cytokines including TNF, IL-1 and IL-6, while up-regulating anti-inflammatory cytokines such as IL-12. Cytokines also can affect the levels of other cytokines, resulting in a cascade effect whereby the other cytokines can mediate the biological level and action of the first cytokine. Because cytokines mediate a wide range of cellular interactions, the ability to manipulate cytokines can be used to alter such interactions in a subject.

CRAs are useful for controlling aberrant cytokine activity associated with various pathologies (see, for example U.S. Pat. No. 5,420,109). A CRA has the general structure: $X_1\text{-}X_2\text{-}(D)Phe\text{-}Arg\text{-}(D)Trp\text{-}X_3$, wherein

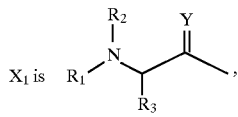

H, COCH$_3$, or absent;

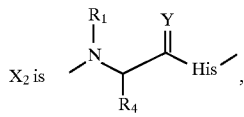

H, His or COCH$_3$; and

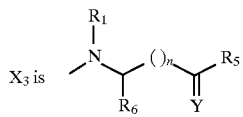

or $R_5$;
wherein Y is O, H$_2$ or S; $R_1$ is H, COCH$_3$, C$_2$H$_5$, CH$_2$Ph, COPh, COO-t-butyl, COOCH$_2$Ph, CH$_2$CO— (polyethylene glycol) or A; $R_2$ is H, COCH$_3$, C$_2$H$_5$ or CH$_2$Ph; $R_3$ is a linear alkyl group having 1 to 6 carbon atoms or a branched or cyclic alkyl group having 3 to 6 carbon atoms; $R_4$ is $(CH_2)_m$—CONH$_2$, $(CH_2)_m$—CONHR$_1$ or $(CH_2)_m$—CONHA; $R_5$ is OH, OR$_3$, NH$_2$, SH, NHCH$_3$, NHCH$_2$Ph or A; and $R_6$ is H or $R_3$; and wherein "Ph" is C$_6$H$_5$; "m" is 1, 2 or 3; "n" is 0, 1, 2 or 3; and "A" is a carbohydrate having the general formula:

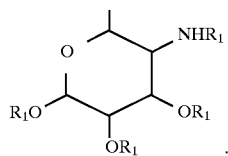

Amino acids are indicated herein by their commonly known three letter codes; "Nle" is the three letter code for norleucine. "(D)" designates an amino acid having a (D)-conformation as compared to the naturally occurring (L)-conformation. Where no specific configuration is indicated, one skilled in the art would understand the amino acid to be an (L)-amino acid. Peptides are shown with the amino terminus (N-terminus) to the left and carboxyl terminus (C-terminus) to the right as is conventional in the art.

A CRA is characterized, in part, by a core structure having the amino acid sequence, (D)Phe-Arg-(D)Trp, or an analog of (D)Trp. A CRA can have a modified amino terminus such as an acetylated N-terminus. A CRA also can have a modified carboxyl terminus such as an amidated C-terminus. A CRA can have a structure where $R_1$ is selected from the group consisting of C$_2$H$_2$ and CH$_2$Ph, and where $R_2$ is selected from the group consisting of H and COCH$_3$. A CRA also can have the structure where $R_1$ and $R_2$ are the same moiety, selected from the group consisting of H, C$_2$H$_5$ and CH$_2$Ph. A CRA can have a structure where $X_1$ is selected from the group consisting of norleucine, norvaline, leucine and isoleucine. A CRA also can have a structure were $R_5$ is covalently bound to $X_1$ such that a cyclic peptide is formed. Methods for synthesizing CRAs are described in U.S. Pat. No. 5,420,109. Representative examples of CRAs include:

(D)Phe-Arg-(D)Trp;
His-(D)Phe-Arg-(D)Trp;
His-(D)Phe-Arg-(D)Trp-Gly;
Gln-His-(D)Phe-Arg-(D)Trp-Gly;
Ac-Nle-Gln-His-(D)Phe-Arg-(D)Trp-Gly-OH;
Ac-Nle-Gln-His-(D)Phe-Arg-(D)Trp-Gly-OC$_2$H$_5$;
Ac-Nle-Gln-His-(D)Phe-Arg-(D)Trp-Gly-NH-NH$_2$;
Ac-Nle-Asn-His-(D)Phe-Arg-(D)Trp-Gly-NH$_2$;
Ac-Nle-Asn-His-(D)Phe-Arg-(D)Trp-Gly-OH;
Ac-Nle-Gln-His-(D)Phe-Arg-(D)Trp-Gly-NHCH$_2$CH$_2$Ph;
Ac-Nle-Gln-His-(D)Phe-Arg-(D)Trp-Gly-NHCH$_2$Ph;

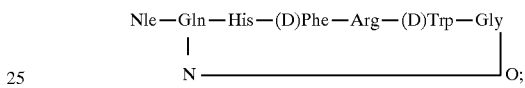

Ac-Gln-His-(D)Phe-Arg-(D)Trp-Gly-NH$_2$;
Ac-Nle-Gln-His-(D)Phe-Arg-(D)Trp-NH$_2$;
Ac-His-(D)Phe-Arg-(D)Trp-Gly-NH$_2$;
His-(D)Phe-Arg-(D)Trp-NH$_2$;
Ac-His-(D)Phe-Arg-(D)Trp-OH; and
Ac-His-(D)Phe-Arg-{(D)Trp(CH$_2$)}-(NAc)Gly-NH$_2$,
wherein {(D)Trp(CH$_2$)} is an analog of (D)Trp, where H$_2$ replaces the α-carbonyl oxygen and (NAc)Gly is a glycine derivative with an N-acetyl moiety.

A particularly useful CRA, designated CRA-1, has the amino acid sequence Ac-Nle-Gln-His-(D)Phe-Arg-(D)Trp-Gly-NH$_2$ (designated "CRA-1" and which is disclosed in U.S. Pat. No. 5,420,109, wherein it is referred to as "EX-2").

The present invention provides a composition comprising an ion exchange resin and a therapeutically active biopolymer in a form for oral administration, wherein the therapeutically active biopolymer can be a nucleic acid, a peptide such as a CRA, a polypeptide or a protein. One skilled in the art would know that the choice of a therapeutically active biopolymer depends on the desired therapeutic effect. Having selected a therapeutically active biopolymer, the skilled artisan can further select an ion exchange resin based on the physical and chemical characteristics of the selected biopolymer.

An ion exchange resin is a porous material having an ionic functional group that can bind a therapeutically active biopolymer. An ion exchange resin can be selected based on matrix composition or structure, chemical type, degree of cross-linking, ionic form, porosity, number of reactive sites or particle size. For example, an ion exchange resin can have a matrix composition of cross-linked agarose, silica, cellulose or polystyrene divinyl benzene.

Ion exchange resins are available from commercial sources, including, for example, Rohm and Haas (Cherry Hill, N.J.), Bio-Rad (Hercules, Calif.), Dow Corning (Midland, Mich.), Pharmacia (Piscataway, N.J.), PerSeptive Biosystems (Cambridge, Mass.), TosoHaas (Montgomeryville, Pa.), Dionex (Sunnyvale, Calif.) and Vydac/The Separations Group (Hesperia, Calif.).

Ion exchange resins are available in different charge densities, porosities and sizes. Such parameters directly affect the loading of the biopolymer on the ion exchange resin and the release characteristics of the biopolymer from the ion exchange resin. Generally, as the charge density of the ion exchange resin increases, the amount of biopolymer that can bind to an ion exchange resin increases. As the porosity of the ion exchange resin decreases, the rate of release generally decreases, which can lead to increased protection from a degradative enzyme. As a further general rule, as the particle size of the ion exchange resin increases, the rate of release decreases. A skilled artisan can select an appropriate combination of these parameters to achieve the desired protection and release characteristics for the biopolymer.

The ionic functional group of an ion exchange resin can be positively or negatively charged. The degree of ionization depends on the pH of the environment of the ion exchange resin. An anion exchange resin, for example, contains positively charged functional groups such as quaternary amino groups. Examples of anionic exchange resins include Q-Sepharose (Pharmacia), Poros Q Strong Anion (Perceptive Biosystems), Toyopearl Super Q-650M (TosoHaas) and Macroprep Q (Bio-Rad).

In comparison, a cation exchange resin contains negatively charged functional groups such as carboxylic acid or sulfonic acid groups. Examples of cation exchange resins include Dionex Ionpac resins CS12 or CS10 (Dionex) or Amberlite® IRP-64 (Rohm and Haas).

The choice of a ion exchange resin will depend on the particular biopolymer used in the composition of the invention. For example, a therapeutically active biopolymer such as an oligonucleotide, which contains a negative charge at physiological pH, can bind to an anion exchange resin such as Duolite® AP-143 (Rohm and Haas). In comparison, a positively charged biopolymer such as a CRA can bind to a cation exchange resin. An amphipathic biopolymer can bind to an anion exchange or a cation exchange resin as desired.

Some particularly useful cation exchange resins to formulate a composition of the invention are the Amberlite® resins (Rohm and Haas) because they are approved for pharmaceutical use by the FDA. For example, Amberlite® IRP-69("IRP-69") is an insoluble, strongly acidic cation exchange resin that is suitable for pharmaceutical applications. IRP-69 consists of particles that range in size from 25–150 $\mu$m, with a mean particle size of 100 $\mu$m. The total cation exchange capacity of IRP-69 is at least 4.3 meq/g.

Amberlite® IRP-64 ("IRP-64") is a cation exchange resin that is particularly useful for protecting a therapeutically active biopolymer such as a CRA from enzymatic degradation (see Example II). IRP-64 is an insoluble, weakly acidic cation exchange resin that is suitable for pharmaceutical applications. IRP-64 consists of particles that range in size from 25–150 $\mu$m, with a mean particle size of 80 $\mu$m. The total cation exchange capacity of IRP 64 is at least 10 meq/g. Thus, a particularly useful composition comprises an ion exchange resin, such as Amberlite® IRP-64, and a therapeutically active biopolymer, such as CRA-1, in a form for oral administration.

Prior to the present invention, it was not known that a composition comprising an ion exchange resin and a therapeutically active biopolymer can form a complex that permits oral administration of the biopolymer. Ion exchange resins have been used in pharmaceutical preparations to deliver small organic drugs (see Ranade, *J. Clin. Pharmacol.*, 31:98–115 (1991), which is incorporated herein by reference). The main contemplated use of such ion exchange resins was to protect the small organic drug from acid-base hydrolysis. In contrast, a biopolymer such as a CPA can be stable in an acid or alkaline environment, but can be degraded in the presence of a degradative enzyme, such as trypsin or chymotrypsin. Thus, a composition of an ion exchange resin and a therapeutically active biopolymer can be useful for protecting the biopolymer from a degradative enzyme.

Additionally, ion exchange resins were used in pharmaceutical preparations for the sustained release of drugs (see, for example, U.S. Pat. Nos. 5,368,852, 4,762,709, 4,308,251 and 4,221,778, each of which are incorporated herein by reference). In contrast, the present invention is directed to protecting a therapeutically effective biopolymer from a degradative enzyme, for example, in the stomach, and releasing the biopolymer in the small or large intestine.

The protection and release of a therapeutically active biopolymer further can be controlled, in part, by selecting an appropriate coating for the composition of the invention. A composition of the invention can be coated to reduce or inhibit release of the biopolymer in a selected region of the gastrointestinal tract. For example, where the biopolymer is a peptide such as a CRA, it is desirable to protect the CRA from proteases such as trypsin or chymotrypsin present in the small intestine. Thus, a composition of the invention can have a coating that is stable to the acidic or degradative conditions in the stomach, but that erodes in the small or large intestine, such that the CRA is released primarily in the large intestine where it can be absorbed into the circulation.

As used herein, the term "coating" means a substance that covers a composition of the invention. A coating can cover a composition completely or partially, thereby allowing gradual, but targeted release of the therapeutically active biopolymer. For example, a coating can be in the form of a solid container for the composition of the invention when the composition is in a liquid form. A coating also can be an erodable coating such as hydroxylpropylmethylcellulose, which erodes slowly as it traverses the small and large intestines, releasing a therapeutically active biopolymer over a period of time. Upon oral administration, an erodable coating can protect the composition while in the stomach and, if desired, the small intestine, but can erode, for example, in the large intestine, thus releasing the ion exchange-biopolymer complex.

An erodable coating also can be an enteric coating, which allows a composition to pass through the stomach without significant alteration, then begins to erode when entering the small intestine. By selecting the thickness or hardness of the erodable coating, the durability of the coating can be adjusted so as to erode completely or partially, and quickly or gradually (see U.S. Pat. No. 4,205,060 and U.S. Pat. No. 3,488,418, each of which is incorporated herein by reference). Thus, an erodable coating can be designed to erode in a selected region of the gastrointestinal tract, thereby providing an additional layer of protection for the biopolymer while in the gastrointestinal tract. Enteric Where a porous ion exchange resin is used to prepare a composition of the invention, a therapeutically active biopolymer can enter a pore and be protected, for example, from degradation due to an enzyme, which is excluded from the pore due to its size. As the complex traverses the gastrointestinal tract, the biopolymer can diffuse from the ion exchange resin, and in the intestine, can be absorbed into the circulation. Since the invention provides compositions in a form for oral administration, the compositions of the invention are particularly useful as medicaments to reduce or inhibit the severity of a pathological condition. Thus, the invention provides a method of reducing or inhibiting the severity of a pathological condition, comprising orally administering a therapeutically effective dose of a composition of the invention.

In one embodiment, the method of the invention can be useful to reduce or inhibit the severity of a condition characterized by altered or aberrant cytokine activity. A therapeutically active biopolymer such as a CRA can regulate aberrant or altered expression of one or more cytokines as occurs in various pathological conditions such as immune responses and inflammatory responses. As disclosed herein, the severity of such conditions can be reduced or inhibited by oral administration of a therapeutically effective dose of a composition comprising an ion exchange resin and one or more CRAs.

A therapeutically effective dose of a composition, in terms of the amount of CRA per body weight, can range from 50 ng/kg to 50 mg/kg, depending on the pathological condition that is being reduced or inhibited. A particularly useful range is 500 ng/kg to coatings are well known in the art and include cellulose acetate phthalate, shellac, wax, ethyl cellulose, hydroxylpropyl cellulose, hydroxylpropyl-methylcellulose phthalate or combinations thereof. An enteric coating can further comprise, for example, microcrystalline cellulose or a plasticizer such as dibutyl phthalate, talc, magnesium stearate, polyethylene glycol, cornstarch or a lubricant. An enteric coating can be particularly useful for coating a composition comprising a CRA and IRP-64 to prevent the release of the CRA in the stomach, where degradative enzymes are present.

The formation of a complex of an ion exchange resin and a therapeutically active biopolymer provides a composition that reduces or inhibits the susceptibility of the biopolymer to degradation. Thus, the invention provides a method of protecting a therapeutically active biopolymer from degradation by forming a complex comprising the biopolymer and an ion exchange resin.

As used herein, the phrase "protecting a therapeutically active biopolymer from degradation" means preserving the therapeutic activity of a biopolymer. Thus, the invention provides a method of protecting the activity of a therapeutically active biopolymer against reduction or inhibition due, for example, to denaturation, cleavage or hydrolysis. In the stomach, for example, degradation of a biopolymer such as a nucleic acid can occur by depurination due to the acidic environment. In the small intestine, degradation of a biopolymer such as a peptide can occur due to the activity of an enzyme such as trypsin or chymotrypsin (see Example II). As disclosed herein, by forming a complex of an ion exchange resin and a peptide, for example, the activity of the peptide is preserved in the presence of digestive enzymes such as trypsin and chymotrypsin, which otherwise would degrade the peptide.

As used herein, the term "complex" when used in reference to an ion exchange resin and a therapeutically active biopolymer means that the biopolymer is associated reversibly with the ion exchange resin. In general, a ion exchange resin-biopolymer complex is formed due to ionic interaction, for example, between a positively charged group on the biopolymer and a negatively charged group on a cation exchange resin. It is recognized, however, that a biopolymer also can adsorb to an ion exchange resin and thereby be protected from degradation.

A particularly useful embodiment is a composition comprising a CRA and a cation exchange resin, where the composition further comprises an enteric coating. When the composition is in the acidic environment of the stomach (see Phillips, Symposium entitled "Current Status on Targeted Drug Delivery to the Gastrointestinal Tract," 11–18 (1993), which is incorporated herein by reference), the enteric coating minimizes release of the CRA from the cation exchange resin. The enteric coating can be selected to begin to erode when entering the small intestine. In the neutral pH environment of the small intestine, the release of CRA from the cation exchange resin is minimal. When the composition reaches the acidic environment of large intestine (between pH 5 and 6), however, the biopolymer is released from the cation exchange resin. The released CRA then can be absorbed across the gastrointestinal epithelium, for example by passive diffusion, and enter the circulation. 5 mg/kg. The ratio of CRA to cation exchange resin can vary from 1:0.001 to 1:1000. However, a particularly useful ratio of CRA to cation exchange resin can be selected based on the charge density of the resin.

As used herein, the term "condition characterized by altered or aberrant cytokine activity" means a physiological state of a subject where the level of activity of a cytokine is greater than or less than the normal physiological level of the cytokine. Such conditions include various pathologies and injuries, including the immune, inflammatory and healing processes associated with an injury. The skilled artisan will recognize that such a condition can be identified by detecting an increased or decreased level or activity of a particular cytokine as compared to the normal level of the cytokine expected in a healthy subject. Methods for determining such normal levels are well known in the art.

Conditions characterized by altered or aberrant cytokine activity include, for example, disuse deconditioning, organ damage such as that which occurs in response to organ transplantation, adverse reactions associated with cancer chemotherapy, diseases such as diabetes or atherosclerosis that are mediated by free radicals or nitric oxide action, and obesity. In particular, altered levels of cytokines are associated with a variety of conditions that lead to disuse deconditioning, such as trauma, casting, denervation, space flight or simulated weightlessness. For example, levels of IL-6 and IL-2 are elevated on the first day of space flight and again after returning from space flight. IL-12 and TNF have been implicated in the rapid decalcification or loss of bone mineral density resulting from immobilization, long term bed rest or spinal cord injury. A CRA can reduce or ameliorate the negative effects associated with disuse conditioning, such as loss of muscle mass, bone density, exercise capacity, oxygen consumption, as well as decreased levels of oxidative or antioxidative enzymes.

Cytokines also play an important role in organ damage and organ protection, significantly affecting such events and conditions as organ transplantation, transplant atherosclerosis, ischemia-reperfusion, cyclosporine-induced nephrotoxicity, myocardial infarction, and stroke. For example, elevated serum levels of TNF and IL-6 can occur in patients undergoing renal, hepatic and cardiac allograft rejection. Organs that can be protected against damage by administering CRAs include, but are not limited to, the heart, kidney, liver, lung, brain, muscle, skin, bone or tissues within these organs. CRAs also can protect against organ damage related to inflammation, atherosclerosis, increases in vascular permeability, fibrosis, necrosis and ischemia-reperfusion, which are associated with elevated levels of IL-1 and TNF.

A CRA also can be used to reduce the negative effects of a cancer chemotherapeutic agent, such as cisplatin, Taxol® or Adriamycin. For example, patients receiving cisplatin have elevated levels of IL-6 and TNF, and patients receiving Taxol® have elevated levels of TNF and IL-1 and enhanced production of TNF in macrophages. Administration of a CRA during cancer chemotherapy can reduce the negative side effects, including but not limited to, nausea, vomiting, mucositis, anorexia, fatigue, and other organ dysfunctions, any or all of which can occur during chemotherapy.

Cytokines and nitric oxide are important mediators in or of diabetes and glomerulonephritis. Nitric oxide and cytokines such as IL-1, IF and TNF regulate beta-cell damage in early insulin-dependent diabetes mellitus. Nitric oxide and cytokines such as IL-1 and TNF also influence the degree of injury resulting from glomerulonephritis. CRAs therefore can be used to treat diabetes and glomerulonephritis.

A CRA also can be useful for decreasing the body weight of a subject, in particular an obese subject. For example, administering a CRA to obese rats resulted in a significant decrease in the rate of body weight gain or a significant decrease in body weight. A CRA also can be useful for increasing the resting oxygen uptake of a subject.

A CRA also can be used to increase the physiologic level of one or more cytokines, including for example, IL-10, in a mammal such as a human. IL-10 can block the activation of some inflammatory cytokines, including TNF, IL-1 and IL-6, while up-regulating cytokines such as IL-12. IL-10 also stimulates the proliferation of mast cells and thymocytes. IL-10 inhibits several monocyte and macrophage functions, including, for example, antigen presentation to T cells, by depressing Class II MHC expression; synthesis of IL-1, IL-6, IL-8, CSF, and TNF; and microbicidal activities. Administration of a CRA also can increase the plasma levels of IL-10 in mammals and, therefore, can be useful for modulating, for example, immunoresponsiveness in a subject.

In addition to the conditions disclosed above, a composition comprising an ion exchange resin and a CRA also can be administered to a subject as a treatment for traumatic injury, bacterial sepsis and related endotoxic shock, inflammation, pain, cachexia, adult respiratory distress syndrome, transplant atherosclerosis, gastrointestinal damage and patho-immunogenic diseases such as arthritis, inflammatory bowel disease, systemic lupus erythematosus and other autoimmune dysfunctions, each of which is characterized by pathologically elevated cytokine activity (see, for example, U.S. Pat. No. 5,420,109). Therefore, the disclosed method of using the composition of the invention is useful for reducing or inhibiting the severity of any of the pathologies and conditions disclosed above.

The following examples are intended to illustrate but not limit the present invention.

EXAMPLE I

Preparation of a Peptide-Ion Exchange Complex

This example provides a method of preparing a peptide-ion exchange resin complex ("complex"). Binding was performed at various ratios of peptide:ion exchange resin and the binding capacity of weak and strong ion exchange resins were compared.

A. Weak Cation Exchange Resin

CRA-1, which has the amino acid sequence Ac-Nle-Gln-His-(D)Phe-Arg-(D)Trp-Gly-NH$_2$, was prepared as described in U.S. Pat. No. 5,420,109, where it is referred to as "EX-2." A 1 mg/ml solution of peptide CRA-1 was prepared by dissolving 19.7 mg CRA-1 in 19.7 ml PBS. Ten mg Amberlite® IRP-69 ("IRP-69") (Rohm and Haas) was added to 5 ml CRA-1 solution (5 mg CRA-1) to achieve a CRA-1:IRP-69 ratio of 1:2. The mixture was adjusted to pH 6.0 and stirred for 2 hr. The suspension then was filtered and the filtrate was analyzed by HPLC (see Example II.A) to determine the total amount of CRA-1 bound to IRP-69. Binding also was performed using CRA-1:IRP-69 ratios of 1:20 and 1:200.

As shown in Table 1, essentially all the CRA-1 is bound to IRP-69 at peptide:resin ratios of 1:20 and 1:200. The relative amount of CRA-1 bound to IRP-69 was 99.63% at a peptide:resin ratio of 1:20, and 99.5% at a peptide:resin ratio of 1:200. At a peptide:resin ratio of 1:2, only 66.91% of the CRA-1 bound to the IRP-69. These results demonstrate that essentially all of a peptide such as CRA-1, which has a net positive charge at pH 6.0, can bind to a weak cation exchange resin such as IRP-69.

TABLE 1

| peptide:resin ratio | CRA-1 bbund to ion exchange resin |
| --- | --- |
| 1:2 | 66.91% |
| 1:20 | 99.63% |
| 1:200 | 99.52% |

B. Strong Cation Exchange Resin

A 1 mg/ml CRA-1 solution was prepared by dissolving 42.5 mg CRA-1 in 42.5 ml PBS. Fifty mg Amberlite® IRP-64 ("IRP-64") (Rohm and Haas) was added to 5 ml CRA-1 solution (5 mg CRA-1) to achieve a peptide:resin ratio of 1:10. The mixture was adjusted to pH 6.0 and stirred for 1 hr. The suspension was filtered and the filtrate was analyzed by HPLC (see Example II.A) to determine the total amount of CRA-1 bound to IRP-64. Binding also was performed using CRA-1: IRP-64 ratios of 1:1, 1:2 and 1:20.

As shown in Table 2, essentially all the CRA-1 is bound to IRP-64 at peptide:resin ratios of 1:10 and 1:20. The relative amount of CRA-1 bound to IRP-64 was 97.55% at a peptide:resin ratio of 1:10, and 98.97% at a peptide:resin ratio of 1:20. When the peptide:resin ratio was 1:1 or 1:2, only 10.48% or 20.08% respectively of the CRA-1 bound to IRP-64. These results demonstrate that essentially all of a peptide such as CRA-1 which has a net positive charge at pH 6.0, can bind to a strong cation exchange resin such as IRP-64.

TABLE 2

| peptide:resin ratio | CRA-1 bound to ion exchange resin |
| --- | --- |
| 1:1 | 10.48% |
| 1:2 | 20.08% |
| 1:10 | 97.55% |
| 1:20 | 98.97% |

EXAMPLE II

The Peptide-Ion Exchange Resin Complex is Protected Against Enzymatic Degradation This example demonstrates that binding CRA-1 to an ion exchange resin stabilizes the peptide against degradation by trypsin and chymotrypsin.

A. Susceptibility of Free Peptide to Enzymatic Degradation

Phosphate buffered saline (PBS) solutions were prepared and adjusted to pH 5.0, 7.0 or 8.0. CRA-1 was dissolved into each of the PBS solutions to a final concentration of 3 mg/ml. Samples of 3 mg/ml trypsin and 3 mg/ml chymotrypsin also were prepared in PBS at pH 5.0, 7.0 or 8.0.

To examine the susceptibility of CRA-1 to trypsin and chymotrypsin, 1 ml CRA-1 solution at pH 5.0 was mixed with 1 ml trypsin solution at pH 5.0 and 1 ml PBS (pH 5.0) to obtain a final concentration of 1 mg/ml CRA-1 and 1 mg/ml trypsin. Similar assay samples were prepared to examine the stability of CPA-1 in trypsin at pH 7.0 or pH 8.0 and in chymotrypsin at pH 5.0, 7.0 or 8.0. As a control, an assay sample was prepared without trypsin or chymotrypsin.

Immediately upon preparing an assay sample, 100 μl of the incubation mixture was removed and the reaction was terminated by adding 100 μl of a Stop solution (90% acetonitrile containing 0.1% trifluoroacetic acid). These samples were analyzed by HPLC to determine the amount of CRA-1 present in each sample at the initiation of the reaction.

The remainder of each assay sample was incubated in an oven at 37° C. At selected times after beginning the incubation, a 100 μl aliquot was withdrawn, the reaction was terminated as described above. The samples were analyzed by HPLC to determine the amount of intact CRA-1.

The HPLC conditions were as follows:
Column: C18, 5 μm, 4.6×250 mm
Mobile phase: 95% A (18% acetonitrile containing 0.1% trifluoroacetic acid) and 5% B (90% acetonitrile containing 0.1% trifluoroacetic acid)
Flow rate: 1.5 ml/min
Detection: UV, 215 nm
Injection volume: 10 μl
Run time: 10 min The amount of CRA-1 remaining at various times after incubation in the presence of trypsin or chymotrypsin at various pH values shows that CRA-1 is stable in the presence of trypsin or chymotrypsin at pH 5.0. However, at pH 7.0 or 8.0, CRA-1 is rapidly degraded, with a half-life of 20–30 minutes by trypsin and by chymotrypsin. These results demonstrate that trypsin and chymotrypsin rapidly degrade a peptide at pH 7.0 or pH 8.0.

B. Stability of a Peptide-Ion Exchange Resin Complex to Enzymatic Degradation

A CRA-1:IRP-64 complex was prepared as described in Example I and isolated by filtration. Fifty mg or 100 mg of the complex was suspended in 5 ml of PBS (pH 7.0) containing either 1 mg/ml trypsin or 1 mg/ml chymotrypsin. The suspensions were rotated at 200 rpm in an incubator at 37° C. for 2 hr. Following incubation, the suspension was vacuum-filtered and the filtrate was analyzed by HPLC to determine the amount of CRA-1 bound to the IRP-64.

The complex then was washed with 50 ml water to remove any traces of enzyme and CRA-1 was eluted from the resin by resuspension in 50 ml 2M KCl and incubation at 37° C. After 1 hr, the suspension was vacuum-filtered and the ion exchange resin was washed and filtered a second time with 50 ml 2M KCl. The filtrate and wash were analyzed by HPLC to determine the amount of drug recovered from the ion exchange resin.

As shown in Table 3, unbound CRA-1 in the presence of trypsin or chymotrypsin was almost completely degraded. However, when CRA-1 is bound to IRP-64, substantial amounts of nondegraded CRA-1 were recovered. Thus, by forming a peptide-ion exchange complex, enzymatic digestion of the peptide was significantly reduced. For example, when the CRA-1 is bound to IRP-64 at a peptide:resin ratio of 1:20, 56.26% of the CRA-1 is recovered after incubation with trypsin and 28.10% is recovered after incubation with chymotrypsin, compared to 83.48% recovered from the control, which was not exposed to the enzyme. Therefore, these results demonstrate that forming a complex comprising a peptide and an ion exchange resin protects the peptide from enzymatic degradation.

TABLE 3

| Unbound controls: | | | |
|---|---|---|---|
| | enzyme | | CRA-1 remaining |
| | trypsin | | 2.96% |
| | chymotrypsin | | 5.47% |
| CRA-1:IRP-64 Complexes: | | | |
| peptide:resin ratio | enzyme | CRA-1 bound | CRA-1 recovered |
| 1:10 | none | 78.60% | 88.84% |
| 1:20 | none | 96.00% | 83.48% |
| 1:10 | trypsin | 77.54% | 53.63% |
| 1:20 | trypsin | 96.00% | 56.26% |
| 1:10 | chymotrypsin | 82.50% | 20.22% |
| 1:20 | chymotrypsin | 96.42% | 28.10% |

Although the invention has been described with reference to the examples provided above, it should be understood that various modifications can be made without departing from the spirit of the invention. Accordingly, the invention is limited only by the following claims.

We claim:

1. A composition of matter, comprising an ion-exchange resin and an oppositely charged cytokine regulatory agent (CRA) in a form for oral administration, wherein the CRA has the amino acid sequence

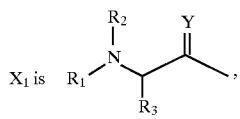

H, COCH$_3$, or absent;

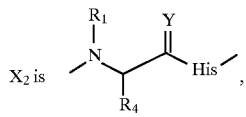

H, His or COCH$_3$; and

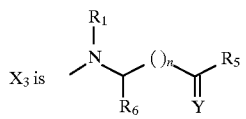

or R$_5$;

wherein Y is O, H$_2$ or S; R$_1$ is H, COCH$_3$, C$_2$H$_5$, CH$_2$Ph, COPh, COO-t-butyl, COOCH$_2$Ph, CH$_2$CO-(polyethylene glycol) or A; R$_2$ is H, COCH$_3$, C$_2$H$_5$ or CH$_2$Ph; R$_3$ is a linear alkyl group having 1 to 6 carbon atoms or a branched or cyclic alkyl group having 3 to 6 carbon atoms; R$_4$ is (CH$_2$)$_m$—CONH$_2$, (CH$_2$)$_m$—CONHR$_1$ or (CH$_2$)$_m$—CONHA; R$_5$ is OH, OR$_3$, NH$_2$, SH, NHCH$_3$, NHCH$_2$Ph or A; and R$_6$ is H or R$_3$; and wherein "Ph" is C$_6$H$_5$; "m" is 1, 2 or 3; "n" is 0, 1, 2 or 3; and "A" is a carbohydrate having the general formula

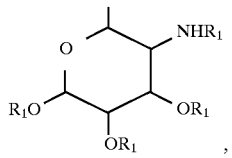

whereby the therapeutic activity of the CRA is protected in the gastrointestinal system against enzymes.

2. The composition of claim 1, wherein the CRA has the amino acid sequence

Ac-Nle-Gln-His-(D)Phe-Arg-(D)Trp-Gly-NH$_2$.

3. The composition of claim 1, wherein the CRA is in an amount that provides a therapeutically effective dose.

4. The composition of claim 1, wherein the ion-exchange resin is a cation-exchange resin.

5. The composition of claim 1, wherein the form for oral administration is a solid form.

6. The composition of claim 5, wherein the solid form is selected from the group consisting of a tablet and a capsule.

7. The composition of claim 1, further comprising a coating.

8. The composition of claim 1, wherein the coating is an erodable coating.

9. The composition of claim 8, wherein the erodable coating is an enteric coating.

10. The composition of claim 8, wherein the erodable coating erodes in the large intestine.

11. A method for protecting a cytokine regulatory agent from degradation in the gastrointestinal system, comprising forming a complex comprising an ion-exchange resin and an oppositely charged cytokine regulatory agent (CRA) having the amino acid sequence $X_1$-$X_2$-(D)Phe-Arg-(D)Trp-$X_3$, wherein

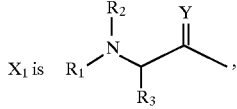

H, COCH$_3$, or absent;

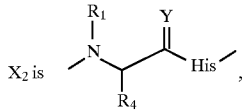

H, His or COCH$_3$; and

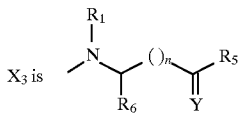

or $R_5$;

wherein Y is O, H$_2$ or S; $R_1$ is H, COCH$_3$, C$_2$H$_5$, CH$_2$Ph, COPh, COO-t-butyl, COOCH$_2$Ph, CH$_2$CO-(polyethylene glycol) or A; $R_2$ is H, COCH$_3$, C$_2$H$_5$ or CH$_2$Ph; $R_3$ is a linear alkyl group having 1 to 6 carbon atoms or a branched or cyclic alkyl group having 3 to 6 carbon atoms; $R_4$ is (CH$_2$)$_m$—CONH$_2$, (CH$_2$)$_m$—CONHR$_1$ or (CH$_2$)$_m$—CONHA; $R_5$ is OH, OR$_3$, NH$_2$, SH, NHCH$_3$, NHCH$_2$Ph or A; and $R_6$ is H or $R_3$; and wherein "Ph" is C$_6$H$_5$; "m" is 1, 2 or 3; "n" is 0, 1, 2 or 3; and "A" is a carbohydrate having the general formula

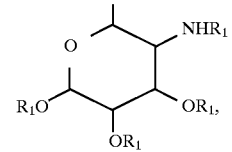

whereby the therapeutic activity of the CRA is protected in the gastrointestinal system against enzymes.

12. The method of claim 11, wherein the CRA has the amino acid sequence

Ac-Nle-Gln-His-(D)Phe-Arg-(D)Trp-Gly-NH$_2$.

13. A method for reducing or inhibiting the severity of a pathological condition, comprising orally administering a therapeutically effective dose of the composition of claim 1 to a subject, thereby reducing or inhibiting the severity of the pathological condition.

14. The method of claim 13, wherein the pathological condition is characterized by altered or aberrant cytokine activity.

* * * * *

UNITED STATES PATENT AND TRADEMARK OFFICE
CERTIFICATE OF CORRECTION

PATENT NO. : 5,846,525  Page 1 of 1
DATED : December 8, 1998
INVENTOR(S) : Maniar and Mauch It is certified that error appears in the above-identified patent and that said Letters Patent is hereby corrected as shown below:

Column 8,
Line 1, replace "CPA" with -- CRA --.

Column 9 through Column 10,
Lines 18 through 11, please move the text beginning "coatings as well" through "circulation" to Column 8, line 54, after "Enteric".

Column 12,
Line 16, please replace "bbund" with -- bound --.

Column 14,
Line 32, please insert -- $X_1$-$X_2$-(D)Phe-Arg-(D)Trp-$X_3$, wherein --.

Signed and Sealed this

Eleventh Day of June, 2002

Attest:

Attesting Officer

JAMES E. ROGAN
Director of the United States Patent and Trademark Office